(12) United States Patent
Codner et al.

(10) Patent No.: US 7,265,844 B2
(45) Date of Patent: Sep. 4, 2007

(54) HORIZONTAL SURFACE PLASMON RESONANCE INSTRUMENT WITH IMPROVED LIGHT PATH

(75) Inventors: Eric P. Codner, Madison, WI (US); Robert M. Corn, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 498 days.

(21) Appl. No.: 10/602,243

(22) Filed: Jun. 24, 2003

(65) Prior Publication Data
US 2004/0201849 A1 Oct. 14, 2004

Related U.S. Application Data

(63) Continuation-in-part of application No. 10/411,583, filed on Apr. 10, 2003, now Pat. No. 7,148,968.

(51) Int. Cl.
*G01N 21/55* (2006.01)

(52) U.S. Cl. ..................................... 356/445

(58) Field of Classification Search ................. 356/445
See application file for complete search history.

(56) References Cited

U.S. PATENT DOCUMENTS

| | | | | |
|---|---|---|---|---|
| 4,775,637 A | * | 10/1988 | Sutherland et al. | 436/527 |
| 4,997,278 A | * | 3/1991 | Finlan et al. | 356/128 |
| 5,262,845 A | * | 11/1993 | Milosevic et al. | 356/445 |
| 5,313,264 A | * | 5/1994 | Ivarsson et al. | 356/73 |
| 6,330,062 B1 | | 12/2001 | Corn et al. | |
| 6,489,102 B2 | | 12/2002 | Corn et al. | |
| 6,570,657 B1 | * | 5/2003 | Hoppe et al. | 356/445 |
| 6,714,303 B2 | * | 3/2004 | Ivarsson | 356/445 |
| 6,862,094 B2 | * | 3/2005 | Johansen | 356/445 |
| 6,879,401 B2 | * | 4/2005 | Gedig | 356/445 |

FOREIGN PATENT DOCUMENTS

JP 63-082346 * 4/1988

OTHER PUBLICATIONS

Lyon, L. Andrew, An Improved Surface Plasmon Resonance Imaging Apparatus, Review of Scientific Instruments, Apr. 1999, vol. 70, No. 4, pp. 2076-2081.

* cited by examiner

*Primary Examiner*—Michael P. Stafira
(74) *Attorney, Agent, or Firm*—Boyle Fredrickson Newholm Stein & Gratz S.C.

(57) ABSTRACT

A surface plasmon resonance imaging apparatus provides an improved optical assembly allowing fixed source and detector operating with a horizontal test surface for a more compact design. In a preferred embodiment, a mechanical linkage of planar mirrors provides a single point adjustment of angle of incidence and angle of refraction while maintaining a constant optical axis of the source and detector.

15 Claims, 2 Drawing Sheets

HORIZONTAL SURFACE PLASMON RESONANCE INSTRUMENT WITH IMPROVED LIGHT PATH

CROSS-REFERENCE TO RELATED APPLICATIONS

This application is a continuation-in-part of U.S. application Ser. No. 10/411,583 filed Apr. 10, 2003 now U.S. Pat. No. 7,148,968 hereby incorporated by reference.

STATEMENT REGARDING FEDERALLY SPONSORED RESEARCH OR DEVELOPMENT

This invention was made with United States government support awarded by the following agency: DOD ARPA F30602-01-2-0555. The United States has certain rights in this invention.

BACKGROUND OF THE INVENTION

The present invention relates to instruments for chemical and biological analyses employing surface plasmon resonance and, in particular, to an instrument having an improved light path that may be easily adjusted.

In surface plasmon resonance, a sensor comprised of a thin metallic film is illuminated by light of an appropriate wavelength and angle of incidence on a "reflecting" side of the film. The energy from the light couples to electrons of the metal of the film creating a resonant condition (surface plasmon resonance) that is highly sensitive to surface conditions on a "sensing" side of the film opposite the side that is illuminated.

Probe molecules may be attached to the sensing side of the metallic film to selectively bind with target molecules in a solution to be analyzed. This binding, through the agency of the electron resonance in the film, causes a drop in reflectance of the reflecting side of the film. Detection of the decrease in reflected light thus provides a sensitive measurement of the binding of target molecules to the probe molecules, in turn providing a sensitive indication of the presence of target molecules in the solution being analyzed.

By placing a variety of different probe molecules on the sensing surface of the film, many different target molecules may be rapidly assessed. Importantly, the target molecules need not be labeled with fluorescent dye or the like prior to analysis.

Current surface plasmon resonance (SPR) equipment can be bulky and difficult to use. Adjustment of the optical system may require separate movement of an analyzing camera and/or light source and possible rotation of the sensing surface. Typically, the sensing surface is oriented vertically, which allows ready access to the optical system for such adjustment, but this vertical orientation can cause problems sealing the flow cells holding the solution to be analyzed against the sensing surface. SPR equipment with a horizontal sensing surface has been constructed to improve access to the sensing surface and improved sealing of the flow cell. The resulting displacement of the camera and light source below the sensing surface, however, complicates adjustment of the camera and light source and undesirably increases the overall height and bulk of the instrument.

BRIEF SUMMARY OF THE INVENTION

The present invention provides a surface plasmon resonance instrument with a horizontal sensing surface but with an optical mechanism that allows the light source and camera to be placed horizontally on either side of the instrument. The optical mechanism may be relatively compact and employ simple planar mirrors to allow one-step adjustment of the angle of incidence and reflectance of light on the sensing surface.

Specifically, the invention provides a horizontal SPR instrument for use with a sample cell having a metallic film with probe molecules attached to a first side of the film, exposable to material flow across the first side of the film, and having a transparent support attached to a second side of the film opposite the first side. The SPR instrument has a support frame with an entrance providing a path for receiving an analyzing light beam along the first fixed axis and an exit providing a path for transmitting a modified light beam along a second fixed axis. A holder supports sample cells with its metallic film oriented horizontally, and an optical assembly adjustably directs the analyzing light beam from the first axis to one of a range of incident angles against the second side of the film and conducts reflected light at a corresponding reflection angle from a second side back along the second axis.

Thus, it is one object of the invention to provide an SPR instrument with a horizontal sampling surface and with a fixed source and detector to provide simplified construction and adjustment of the instrument.

The first and second fixed axes may be substantially aligned and horizontal.

It is another object of the invention to permit the design of a low profile horizontal SPR instrument by displacing the light source and detector to the sides of the sample cell.

The device may include a single operator communicating with the optical assembly to simultaneously change the angle of incidence and reflection by the same amount.

Thus, it is another object of the invention to provide an instrument that may be easily adjusted without the need to separately move the camera and or light source with its attendant optical components.

The device may include a coupling prism having a first prism face adjacent to the second side of the film and receiving from the optical assembly, at a second prism face, the analyzing light beam directed toward the second side of the film, and providing to the optical assembly, through a third prism face, the modified light beam reflected from the second side of the film.

Thus, it is another object of the invention to improve light coupling to the film through the use of a prism element.

The optical assembly may include a correction mechanism adjusting the position of the analyzing light beam incident on the second prism face and correcting the offset of the modified light beam from the third prism face caused by refraction of the light by the prism with different angles of incidence and reflection.

Thus, it is another object of the invention to provide a mechanism that corrects for refractive effects of the prism that may cause misalignment of the optical path.

The optical assembly may be constructed of movable planar mirrors.

Thus it is another object of the invention to provide an optical assembly for an SPR instrument that does not require complex curved mirrors or other lens elements.

The optical assembly may include a first mirror, receiving the analyzing light beam through the entrance along the first axis and directing the analyzing light beam at a third fixed angle to a second mirror that moves about a point near the second side of the film in the holder. The optical assembly may further include a third mirror also movable about the point near the second side of the film in the holder to receive the reflected modified light beam from the second side of the film and directing the modified light beam at a fourth fixed angle to a fourth mirror which in turn transmits the modified light beam to the exit along the second axis.

It is thus another object of the invention to create a folded optical path in which the movement of mirrors, rather than the source and detector, provides changing angles of incidence and reflection.

The second and third mirrors may be mounted on four-bar linkages to adjust a normal angle of the second mirror to substantially halfway between the third fixed angle and an angle of an axis between the second mirror and the second surface on the film and to adjust the normal angle of the third mirror halfway between the fourth fixed angle and an angle of an axis between the third mirror and the second surface on the film.

Thus it is another object of the invention to provide a simple mechanism for providing complex orbiting and tilting motion of mirrors necessary to conduct light between a fixed light source and detector for a variety of needed angles of incidence and reflectance.

The SPR instrument may include an angulation mechanism communicating with the four-bar linkages for swinging the second and third mirrors simultaneously by equal angles about the point on the second side of the film. This mechanism may be a pair of cams adapted to move in unison along the vertical axis, each cam engaging an opposite arm of one of the four-bar linkages of the second and third mirrors to urge them simultaneously to different angulations.

It is thus another object of the invention to provide a simple mechanism for moving the mirrors on the four-bar linkages.

The device may include a tracking mechanism communicating with the first and fourth mirrors to slide the first and fourth mirrors horizontally to direct the light to and from the second and third mirrors, respectively, with movement of the second and third mirrors.

Thus it is another object of the invention to ensure proper optical alignment of the mirrors with angulation of the beams.

The tracking mechanism may be a vertical arm extending from a first mirror to follow the horizontal position of the second mirror, and a second vertical arm extending from the fourth mirror to follow the horizontal position of the third mirror.

It is thus another object of the invention to provide a simple mechanism for tracking the horizontal component of motion of the second and third mirrors.

When the device includes a coupling prism, the first and second vertical arms may provide a profiled camming surface, communicating with the second and third mirrors, respectively, where the profile modifies the relative horizontal location of the second and first mirrors and the relative horizontal location of the fourth and third mirrors with angulation of the second and third mirrors about a point near the second side of the film.

It is thus another object of the invention to provide a simple mechanism for correcting refractive effects of the prism beyond what can be obtained with simple linkages.

These particular objects and advantages may apply to only some embodiments falling within the claims and thus do not define the scope of the invention.

DETAILED DESCRIPTION OF THE PREFERRED EMBODIMENT

Figure 1:
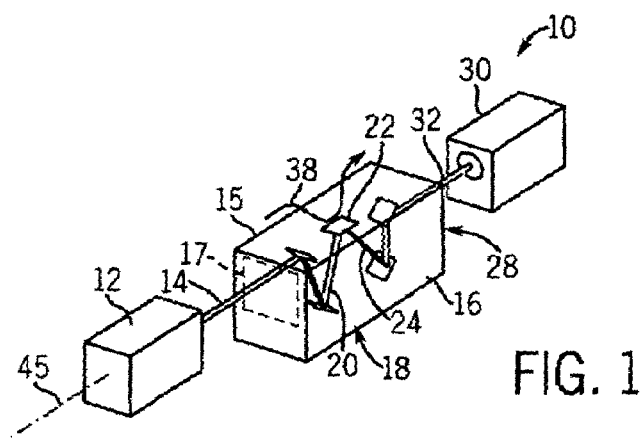
FIG. 1 is a simplified perspective view of the SPR instrument of the present invention showing a fixed light source and detector flanking an optical assembly providing angled incident and reflective light about a horizontal sensing surface.

Referring now to FIG. 1, a horizontal surface plasmon resonance instrument (HSPR) 10, works with a light source 12 providing an analyzing light beam 14 to the analyzer unit 15 where it is modified to become modified light beam 32 and received by camera 30. Both analyzing light beam 14 and modified light beam 32 are coaxial along fixed horizontal axis 44 allowing the light source 12 and camera 30 to be fixed and mounted conveniently to either side of the analyzer unit 15.

The light source 12 may be, for example, a monochromatic coherent or incoherent source including a lamp or laser, filter, polarizer, and lens system of types well known in the art. The light source directs the analyzing light beam 14 toward the analyzer unit where the analyzing light beam 14 enters an entrance area 17 to be received by the optical assembly 18 held by a support frame 16 of the analyzer unit 15. The optical assembly 18 redirects the analyzing light beam 14 to create a first incident beam 20, directed upward against the lower side of a sample cell 22 at an incident angle (by convention measured with respect to a vertical axis 66 normal to a lower surface of the sample cell 22).

Figure 2:
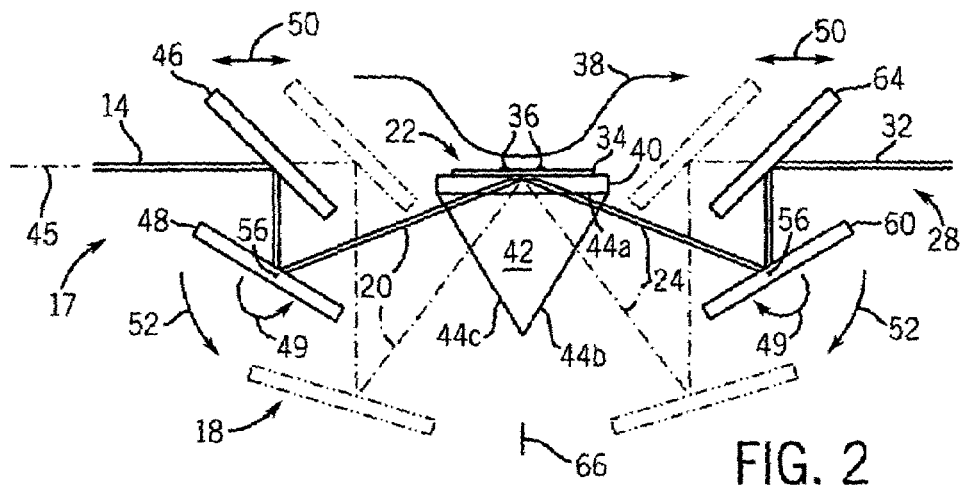
FIG. 2 is an elevational view of the elements of the optical assembly of FIG. 1 showing positioning of upper and lower planar mirrors to provide two different angles of incidence and reflection.

Referring momentarily to FIG. 2, the sample cell 22 may include, for example, a gold film 34 adhered to the top side of a transparent support 40 or the like as is well known in the art. The top surface of the film 34 may receive probe molecules 36, intended to react with materials that will be passed over the surface of the film 34 as indicated by arrow 38 via a flow cell or the like. The incident light beam 20 passes upward through the transparent support 40 striking a center 54 of the lower surface of the film 34.

Referring again to FIG. 1, a reflected beam 24, at a reflection angle equal and opposite to the incident angle, is reflected off the lower surface of the film 34 and is again received by the optical assembly 18 to be redirected as a modified light beam 32 to an exit area 28 as the modified light beam 32 received by the camera 30.

The camera 30 is preferably a digital camera such as employs a charged coupled sensor or the like to produce an electronic image signal that may be analyzed to detect reduced reflection caused by the surface resonance effect. For this reason, the camera 30 is focused on the lower surface of the film 34 to obtain an image therefrom. Similarly, the light source 12 may be focused on the lower surface of the film 34 to provide an even illumination across the area of the film 34.

Referring now to FIG. 2, the optical assembly 18 includes two upper mirrors 46 and 64 aligned generally along the axis 45 and slidable there along on either side of the sample cell 22, and two lower mirrors 48 and 60 mounted generally to orbit about a center 54 located in the center of the lower surface of the film 34, on opposite sides of the center 54.

The analyzing light beam 14 from the light source 12 is received by mirror 46, angled at approximately 45° to the axis 45 to redirect analyzing light beam 14 from the horizontal axis 44, vertically downward to second mirror 48. The second mirror 48 redirects the analyzing light beam 14 toward the center 54 as the incident beam 20.

The incident beam 20 is reflected from the lower surface of the film 34 to become a reflected beam 24. Reflected beam 24 is received by third mirror 60 which redirects the reflected beam 24 vertically upward to the fourth mirror 64. The fourth mirror 64 is angled at 45 degrees to axis 45 (but 90 degrees to the mirror 46) to redirect the received beam along the axis 45 as the modified light beam 32.

As noted, mirrors 48 and 60 may move in orbits 52 symmetrically about the center 54 to provide a range of different angles of incidence and reflection observing the rule that the angle of incidence of the incident beam 20 must be equal to the angle of reflectance of the reflected beam 24 for the range of angles. As they move in orbits 52, mirrors 48 and 60 also rotate 49 about their center pivots 56 and 56', respectively, so as to constantly direct the incident beam 20 and reflected beam 24 toward the center 54.

As mirrors 48 and 60 move, mirrors 46 and 64 may slide in horizontal motion 50 so as to continue to align with mirrors 48 and 60.

Referring still to FIG. 2, the transparent support 40 of the sample cell 22 may abut a base face 44a of an optical prism 42, the prism 42 having base face 44a, a right face 44b, and a left face 44c together whose planes describe an equilateral triangle. The prism 42 provides improved coupling of the light of incident beam 20 and reflected beam 24 to the film 34, passing beam 20 approximately perpendicularly through face 44b and passing beam 24 approximately perpendicularly through face 44a to reduce interface reflections and refraction of the prism 42. Deviations of the angle of passage from perpendicular, as the angles of incidence and reflectance change, cause some refractive effects as will be discussed below. The prism 42 may be a part of the transparent support 40 and replaceable with the film 34 in an alternative embodiment.

Figure 3:
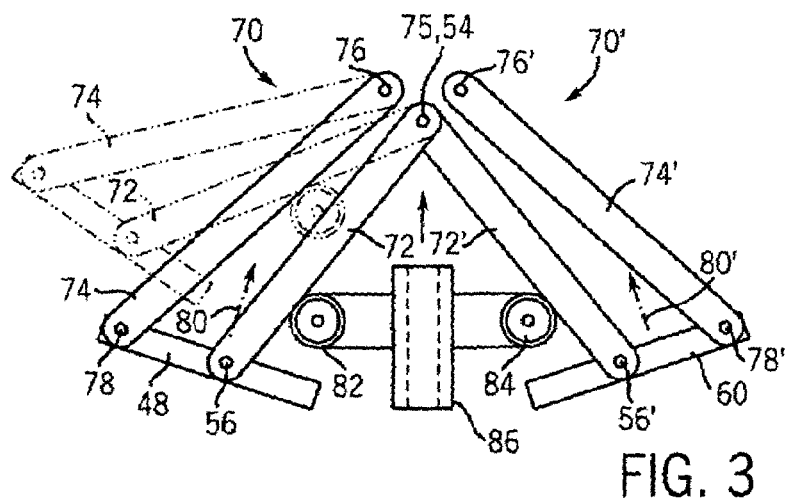
FIG. 3 is a view similar to FIG. 2 showing one four-bar linkage such as holds lower mirrors of FIG. 2 for orbit about the sensing surface as moved by a roller assembly.

Referring now to FIGS. 2 and 3, the orbits 52 and rotations 49 of mirrors 48 and 60 is provided by a four-bar linkage 70 and 70' supporting mirrors 48 and 60, respectively to provide necessary the orbits 52 and rotation 49. Each four-bar linkage 70 and 70' is duplicated on both front and rear sides of the sample cell 22 and mirrors 48 and 60 so as to be displaced from the light path while providing the necessary support for the mirrors 48 and 60.

Each four-bar linkage 70 and 70' includes a lower bar 72, 72' and an upper bar 74, 74'. Each of the lower bars 72, 72' pivots about a common pivot point 75 on the support frame 16, aligned with center 54 as shown in FIG. 2. The remaining ends of lower bars 72, 72' pivotally attach to the center pivots 56, 56' of the mirror 48. The upper bars 74, 74' are generally of different length than lower bar 72, 72' and extends from secondary pivot point 76, 76' on a side wall of the support frame 16, removed from common pivot point 75.

The remaining ends of upper bars 74, 74' attach to outer edges of mirrors 48 and 60 at edge pivots 78, 78'.

The length and orientation of the elements of four-bar linkages 70 and 70' are adjusted according to methods well known in the art, to provide the necessary rotations 49 during the orbits 52 of the mirrors 48 and 60 so that a normal 80, 80', of the mirrors 48 and 60, respectively, approximately bisects an angle formed between a first line intersecting center pivot 56, 56', and center 54 and a second line extending vertically from center pivots 56, 56'.

Simultaneous and equal movement of four-bar linkages 70 and 70' and thus mirrors 48 and 60 is accomplished by means of a pair of rollers 82 and 84 which ride against the lower edges of lower bars 72 and 72' and which are held by a vertical slide 86, which with upward motion, such as may be provided by a micrometer mechanism or the like (not shown), causes upward motion of the rollers 82 and 84 raising lower bars 72 and 72' equally and oppositely about common pivot point 75. The slide 86 is supported on a side wall of the support frame 16. It will be understood that motion of the slide 86 provides a single point of adjustment, thereby providing complete control of the angulation without the need to move the light source 12, or camera 30, or make other adjustments in the optical assembly.

Figure 4:
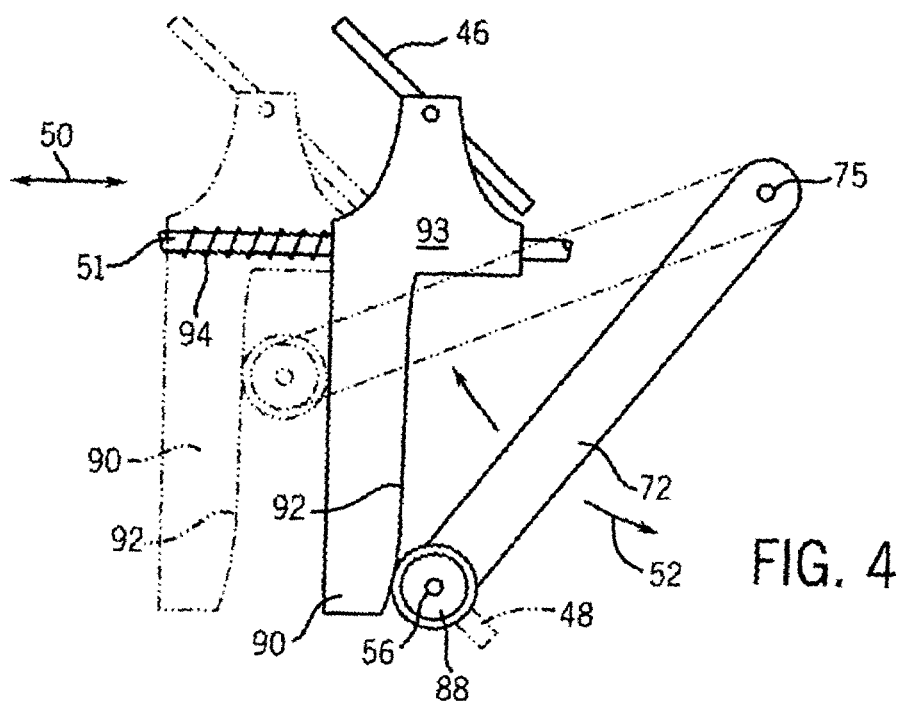
FIG. 4 is an elevational fragmentary view similar to that of FIG. 2 showing a tracking mechanism for moving the upper mirrors of FIG. 2 with motion of the four-bar linkages of FIG. 3.

Referring again to FIGS. 2 and 4, mirrors 46 and 64 must move horizontally to transmit or receive light from their respective mirrors 48 and 60 with orbital motion of mirrors 48 and 60. This is accomplished by means of a roller 88 positioned at the center pivots 56 and 56' on lower arms 72 and 72'. Only lower arm 72 is shown for clarity, however, it will be understood from the following description that the same mechanism is applied in mirror symmetric fashion with respect to the mirror 64.

The roller 88 engages an inner camming surface 92 of a vertical arm 90. The vertical arm 90 in turn extends downward from a sliding mirror support 93 supported for horizontal motion 50 on a slideway 51. The mirror support 93 holds the mirror 46 allowing it to move with the vertical arm 90 against a helical compression spring 94 urging the mirror support 93 rightward. The helical compression spring 94 biases the inner camming surface 92 leftward against the roller 88 to move therewith. With upward angulation of the lower bar 72, roller 88 rides against the camming surface 92 sliding the sliding mirror support 93 leftward so that the mirror 46 is always positioned above mirror 48 with orbit 52 of the mirror 48. As mentioned, a similar arrangement with mirror symmetry is used for mirrors 60 and 64.

Figure 5:
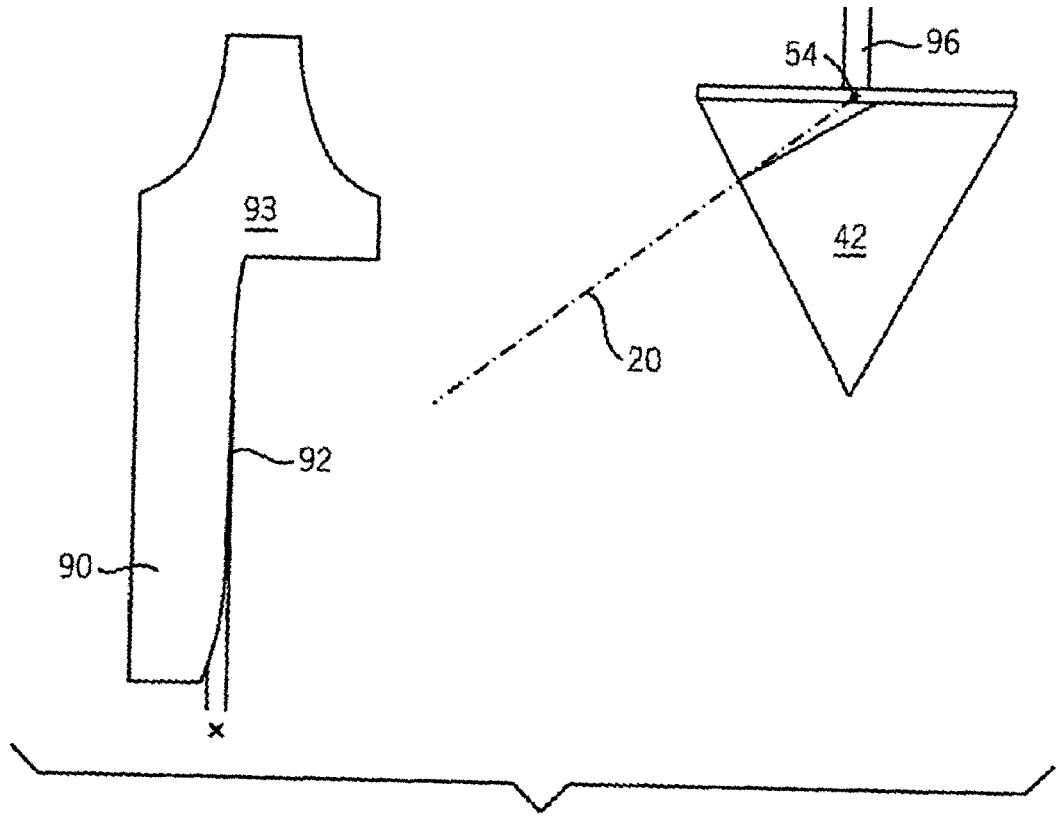
FIG. 5 is an enlarged view of a downward arm of the tracking mechanism of FIG. 4 showing a curvature that causes additional motion to correct for refractive effects.

Referring now to FIG. 5 at different angulations of the incident beam 20, a slight refractive effect will occur within prism 42 causing a displacement 96 of the center of the incident beam 20 with respect to the center 54. This can be corrected by a slight motion of mirror 46 to advance or retard it in its following of mirror 48. This advance and retard is provided by a slight tapering of camming surface 92 which may overlay a minor arbitrary functional dependence of the horizontal position of the mirror 46 as a function of the orbital angle of mirror 48. A similar arrangement with mirror symmetry is used for mirrors 60 and 64.

It will be understood that motion of the slide 86 provides a single point of adjustment, thereby providing complete control of the angulation of the incident beam 20 and the reflected beam 24 and all the mirrors 46, 48, 60, and 64 without the need to move the light source 12, or camera 30, or make other adjustments in the optical assembly.

It is specifically intended that the present invention not be limited to the embodiments and illustrations contained herein, but include modified forms of those embodiments including portions of the embodiments and combinations of elements of different embodiments as come within the scope of the following claims.

We claim:

1. A horizontal surface plasmon resonance instrument for use with a sample cell having a metallic film with probe molecules attached to a first side of the film exposable to material flow across the first side of the film and having a transparent support attached to a second side of the film opposite the first side, the horizontal surface plasmon resonance instrument comprising:
   a support frame having:
   a) an entrance providing a path for receiving an analyzing light beam along a first fixed axis;
   b) an exit for providing a path for transmitting a modified light beam along a second fixed axis; and
   a holder for supporting the sample cell with the metallic film in a horizontal orientation;
   an optical assembly for adjustably directing the analyzing light beam received along the first fixed axis at one of a range of incident angles at the second side of a film of a sample cell in the holder and for directing reflected light received at a corresponding one of a range of reflection angles from the second side of the film back along the second fixed axis.

2. The horizontal surface plasmon resonance instrument of claim 1 wherein the first fixed axis and the second fixed axis are substantially aligned and horizontal.

3. The horizontal surface plasmon resonance instrument of claim 1 including a single operator communicating with the optical assembly to simultaneously change the angle of incidence and reflection by the same amount.

4. The horizontal surface plasmon resonance instrument of claim 1 including a coupling prism having a first prism face adjacent to the second side of the film and receiving from the optical assembly at a second prism face the analyzing light beam directed toward the second side of the film and, providing to the optical assembly through a third prism face, the modified light beam reflected from the second side of the film.

5. The horizontal surface plasmon resonance instrument of claim 1 wherein the optical assembly includes a correction mechanism adjusting the position of the analyzing light beam incident on the second prism face and correcting the offset of the modified light beam from the third prism face caused by refraction of the prism with different angles of incidence and reflection.

6. The horizontal surface plasmon resonance instrument of claim 1 wherein the optical assembly is constructed of movable planar mirrors.

7. The horizontal surface plasmon resonance instrument of claim 6 wherein the optical assembly includes a first mirror receiving the analyzing light beam through the entrance along the first axis and directing the analyzing light beam at a third fixed angle to a second mirror moving about a point near the second side of the film in the holder; and
   wherein the optical assembly further includes a third mirror movable about the point near the second side of the film in the holder to receive the reflected modified light beam from the second side of the film and directing the modified light beam at a fourth fixed angle to a fourth mirror transmitting the modified light beam to the exit along the second axis.

8. The horizontal surface plasmon resonance instrument of claim 7 wherein the second and third mirrors are mounted on four-bar linkages to adjust a normal angle of the second mirror to substantially halfway between the third fixed angle and an angle of an axis between the second mirror and the second surface of the film, and to adjust a normal angle of the second mirror to substantially halfway between the fourth fixed angle and an angle of an axis between the center of the third mirror and the point near the second surface of the film.

9. The horizontal surface plasmon resonance instrument of claim 8 including an angulation mechanism communicating with the four-bar linkages for swinging the second and third mirrors simultaneously by equal angles about the point on the second side of the film.

10. The horizontal surface plasmon resonance instrument of claim 9 wherein the angulation mechanism is a pair of cams adapted to move in unison along a vertical axis each cam engaging an opposite arm of one of the four-bar linkages of the second and third mirrors to urge them simultaneously to different angulations.

11. The horizontal surface plasmon resonance instrument of claim 7 including a tracking mechanism communicating with the first and fourth mirrors to slide the first and fourth mirrors horizontally to conduct the light to and from the second and third mirrors with movement of the second and third mirrors.

12. The horizontal surface plasmon resonance instrument of claim 11 wherein the tracking mechanism a first vertical arm extending from the first minor to follow the horizontal position of the second mirror and a second vertical am1 extending from the fourth mirror to follow the horizontal position of the third mirror.

13. The horizontal surface plasmon resonance instrument of claim 11 including a coupling prism having a first prism face adjacent to the second side of the film and receiving from the optical assembly at a second prism face, the analyzing light beam directed toward the second side of the film and providing to the optical assembly through a third prism face the modified light beam reflected from the second side of the film;
   wherein the first and second vertical arms provide a camming surface communicating with the second and third mirrors, respectively, and wherein the camming surfaces are profiled to modify the relative horizontal location of the first 10 and second mirrors and the fourth and third mirrors with angulation of the second and third mirrors about the point near the second side of the film;
   hereby refractive effects of the prism with angulation of the incident and reflected light may be corrected.

14. The horizontal surface plasmon resonance instrument of claim 1 including light source directing the analyzing light beam along the first fixed axis and a camera receiving the modified light beam along the second fixed axis.

15. The horizontal surface plasmon resonance instrument of claim 1 wherein the holder supports the sample cell with the first side of the film facing upward.

* * * * *